United States Patent [19]

LeFevre

[11] Patent Number: 4,997,420
[45] Date of Patent: Mar. 5, 1991

[54] PORTABLE DRUG DELIVERY DEVICE INCLUDING PUMP WITH TAPERED BARREL

[76] Inventor: Robert J. LeFevre, 4626 Kathi Dr., Bethlehem, Pa. 18017

[21] Appl. No.: 458,506

[22] Filed: Dec. 28, 1989

[51] Int. Cl.$^5$ .............................................. A61M 1/00
[52] U.S. Cl. ................................... 604/121; 604/135; 604/246; 128/DIG. 12
[58] Field of Search ................................... 604/51–53, 604/93, 118, 121, 122, 126, 134, 135, 181, 186, 207, 219, 236, 246; 128/DIG. 12

[56] References Cited

U.S. PATENT DOCUMENTS

| | | |
|---|---|---|
| 3,245,591 | 4/1966 | Kneusel et al. |
| 3,451,393 | 6/1969 | Sarnoff ............................ 604/135 |
| 4,210,173 | 7/1980 | Choksi et al. ..................... 137/512.3 |
| 4,615,694 | 10/1986 | Raines ............................... 604/126 |
| 4,741,733 | 5/1988 | Winchell et al. ................. 604/51 |
| 4,813,937 | 3/1989 | Vaillancourt ..................... 604/131 |

Primary Examiner—John D. Yasko
Assistant Examiner—Adam J. Cermak
Attorney, Agent, or Firm—Shoemaker and Mattare, Ltd.

[57] ABSTRACT

A portable drug delivery device for delivering a drug in liquid or fluid form at a constant and self-regulated rate to a patient comprises a syringe having spring loaded piston reciprocal in a cylinder having a reverse taper to pressurize the drug to be dispensed. The reverse taper on the cylinder results in decreasing friction on the piston as the piston moves in the cylinder during a dispensing cycle, and is designed to compensate for the decreasing force exerted on the piston by the expanding spring. A length of tubing connected to the syringe conveys the drug to a needle or other device for administering the drug to a patient, and a restrictor in the length of tubing impedes flow of the drug to achieve a desired flow rate. The restrictor may be sized to achieve any desired flow rate, and in a preferred form of the invention comprises a laser-burned hole in a fitting attached to the outlet end of the length of tubing.

8 Claims, 5 Drawing Sheets

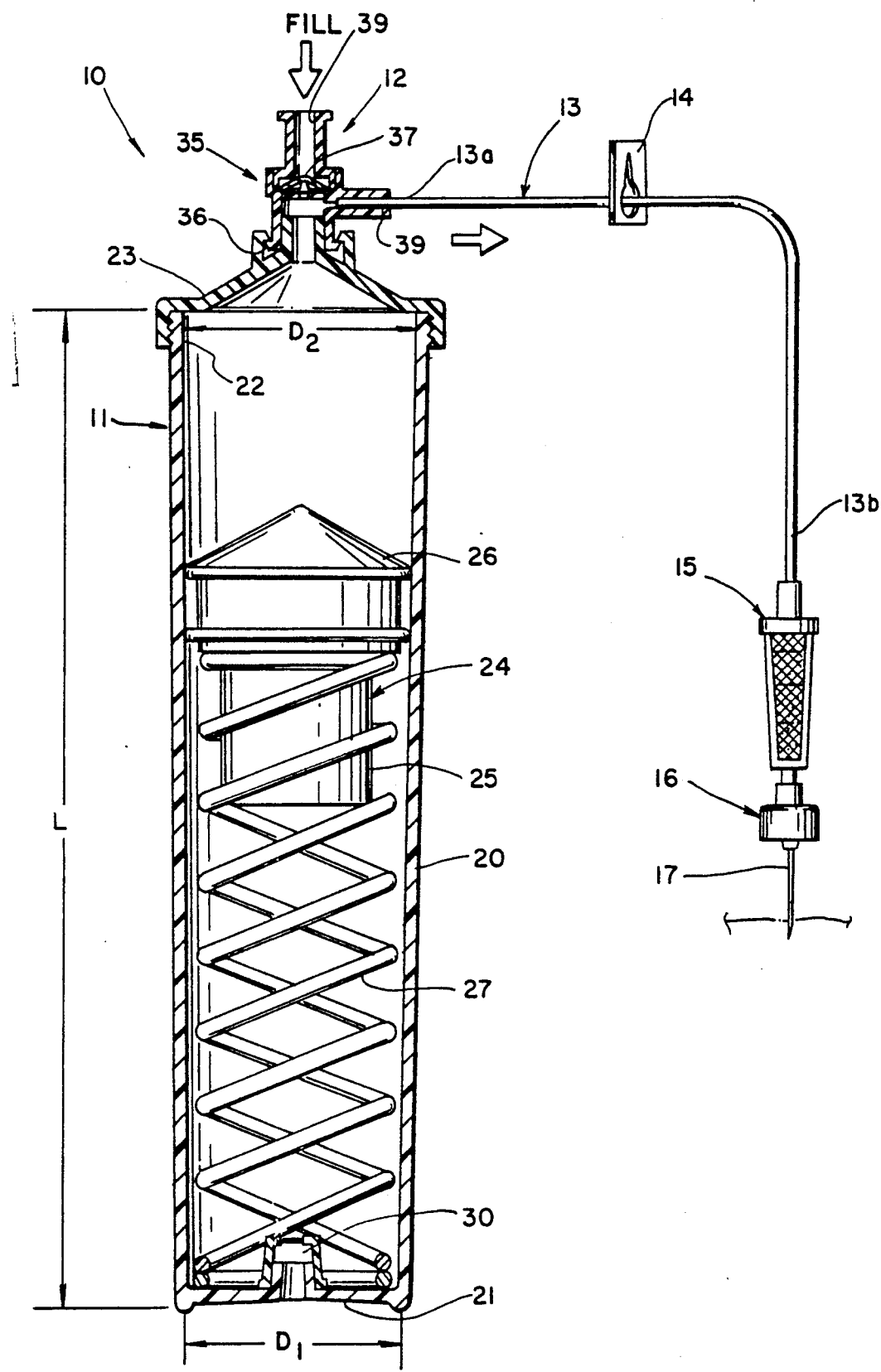

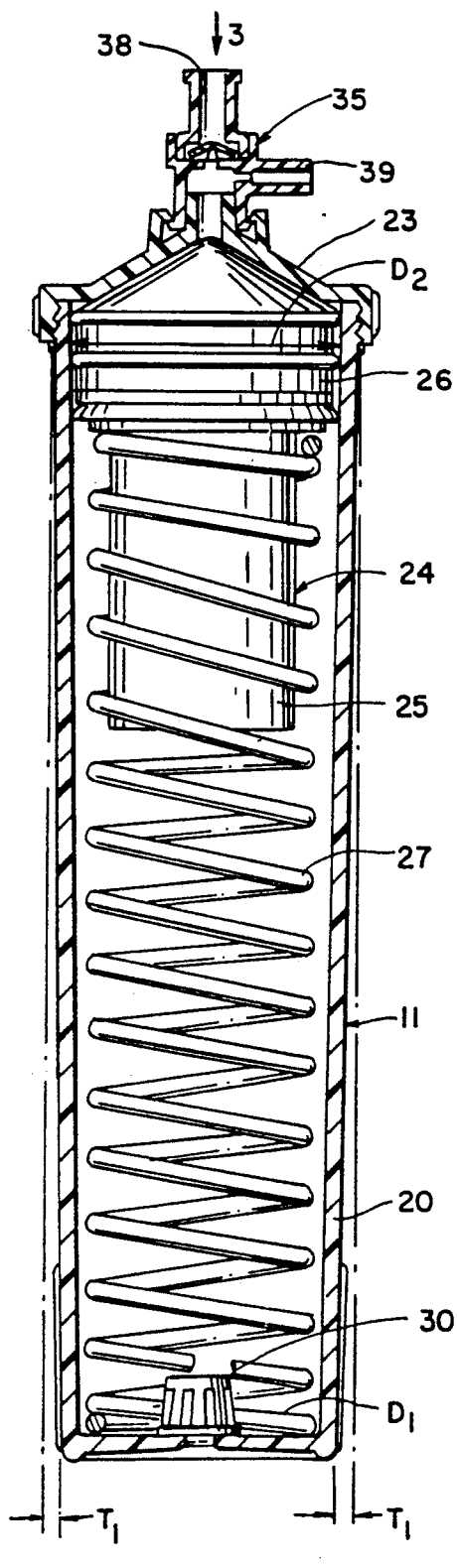
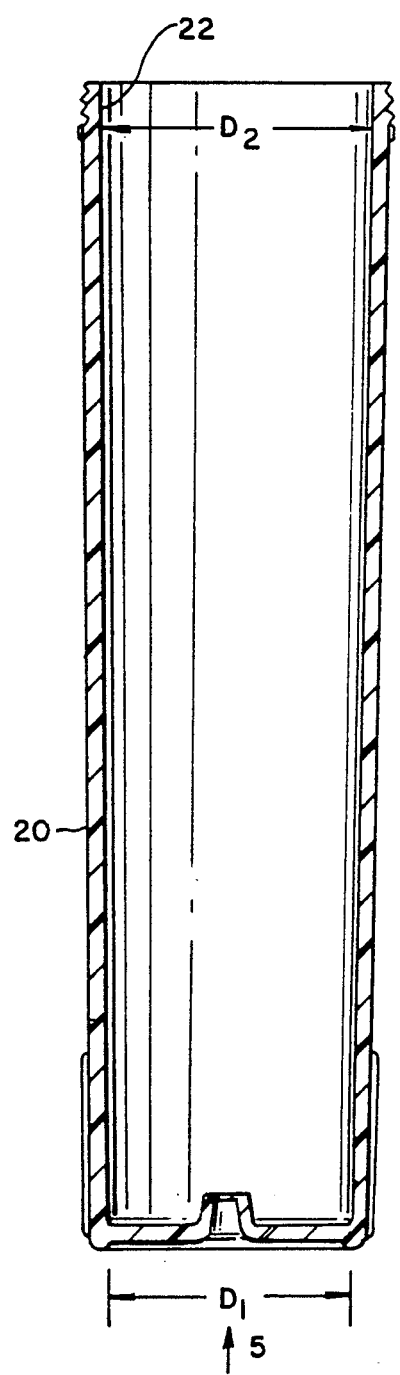

PORTABLE DRUG DELIVERY DEVICE INCLUDING PUMP WITH TAPERED BARREL

FIELD OF THE INVENTION

This invention relates to drug delivery devices for administering drugs to a patient. More particularly, the present invention relates to a portable drug delivery device which delivers a constant flow rate of drugs in liquids or fluids to the ambulatory patient.

DESCRIPTION OF THE PRIOR ART

Medical science and therapeutics have evolved in their efficient delivery of drugs and medicines to those afflicted with disease, chronic illnesses and disabilities to the point where delivery systems are capable of being portable. For the patients undergoing care and treatment, they no longer are rendered immobile but can continue to work, travel and generally enjoy a more normal life style while being treated. In those instances where prolonged drug administration is desirable, continuous drug flows and infusions at low rates are beneficially effected with good results. Many different types of apparatus exist in the prior art for administering medication to such patients, including battery powered miniature pumps, hypodermic syringes, implanted reservoirs and dosing devices, and the like. Some of these devices are capable of automatically or responsively administering a pre-regulated quantity of drug over a period of time. However, many of these prior art devices are relatively complex and expensive in construction, and/or not always capable of delivering a truly dependable and constant rate of medication over the entire dosage period. For instance, some of the prior art devices are constructed so that they may administer a greater quantity of the drug at the beginning of a dosage cycle than at the end of the cycle to the detriment of the patient. Others are relatively large and cumbersome and are not easily accessible once implanted while being used, or are not truly portable, in that the patient is severely restricted in his movements during use of the device.

Many prior art devices of the type described above use the process of pressuring the drug to be administered to the patient, employing elastomeric chambers to hold the drug. Unfortunately, such devices tend to exert a greater pressure on the drug at the beginning of a dispensing cycle as compared to the end resulting in uneven dosage administration. Further, contact between the elastomeric chamber wall and the medication often presents a danger of contamination of the medication in unsterile environment. Other devices use other means such as pistons, springs or pretensioned elastomeric biasing means for pressurizing the medication. For example, conventionally shaped hypodermic syringes use a spring-propelled piston in a barrel. The barrel is generally cylindrical in configuration, having a straight wall. As the piston moves forward in the barrel, it is subjected to frictional drag. Regulation of the flow of medication in these devices is achieved by the cooperative interaction between the force exerted by the piston on the medication and the impeding action to flow produced by a restrictor on the discharge side of the chamber. Consequently, as the spring expands and exerts less force on the piston, the frictional resistance to movement of the piston adversely affects the pressure exerted on the medication being dispensed, resulting in an unwanted changing flow rate as the dispensing cycle progresses. In other words, as the pressure varies and changes during a dispensing cycle, so does the flow rate.

Examples of some prior art devices are disclosed in prior U.S. Pat. Nos. 3,895,631, 4,318,400, 4,597,754, 4,741,733, 4,755,172 and 4,813,937.

A drug delivery system which is portable, compact and accessible, simple and economical to make and use, and which is dependable and achieves a constant and predictable flow of drug during its delivery cycle is desired.

SUMMARY OF THE INVENTION

Accordingly, it is an object of the present invention to provide a drug delivery device for administering medication to a patient at a constant predictable and regulable rate during a dosage or dispensing cycle.

Another object of the invention is to provide a portable drug delivery system for delivering a drug to a patient at a constant and predetermined flow rate.

A further object of the invention is to provide a pump of the type having a spring-biased piston in a cylinder for pressurizing a liquid or fluid material to be delivered, wherein the cylinder has a reverse taper to relieve frictional resistance between the piston and cylinder as the spring expands, thereby achieving a balance between the decreasing force exerted by the expanding spring and the frictional drag on the piston, obtaining an essentially constant pressure on the material during an entire dispensing cycle.

Yet another object of the invention is to provide a restrictor for regulating the flow rate of a drug delivery system which is economical to manufacture, simple, requires fewer parts and is easier to assemble than prior art devices.

These as well as other objects and advantages of the invention are accomplished by a device in which a pump means for pressurizing the drug to be delivered is connected with conduit means for conveying the pressurized drug in liquid form to the patient, and including restrictor means for regulating the flow rate of drug pressurized by the pump means and conveyed by the conduit means, said pump means having means for maintaining a constant pressure on the drug during an entire dispensing cycle to thereby obtain a constant flow rate of the drug during the dispensing cycle. More specifically, the device comprises a syringe having a spring loaded piston reciprocating in a cylinder having a reverse taper to pressurize the drug to be dispensed in liquid form. The reverse taper on the cylinder results in decreasing friction on the piston as the piston moves in the cylinder during a dispensing cycle, and is designed to compensate for the decreasing force exerted on the piston by the expanding spring. A length of tubing connected to the syringe conveys the drug to a needle or other device for administering the drug to a patient, and a restrictor in the length of tubing impedes flow of the drug to achieve a desired flow rate. The restrictor may be sized to achieve any desired flow rate, and in a preferred form of the invention comprises a laser-burned hole in a fitting attached to the outlet end of the length of tubing. The size of the restrictor and the force exerted by the spring-loaded piston are interrelated to achieve the desired flow rate, with the restrictor being selectively sized to achieve a desired flow rate, depending upon the amount of medication to be administered to the patient in a given time period.

A one-way valve on the syringe enables it to be filled with medication to be subsequently dispensed, and a slide clamp or other device may be provided in association with the length of tubing to interrupt flow when desired. A cone filter may also be associated with the length of tubing to filter out contaminants, and the laser-burned hole may be provided in the housing of the cone filter.

The tubing, in which the restrictor is positioned, may be constructed of any rigid or semi-rigid material such as glass, hardened acrylic resinous materials, plastics and the like.

BRIEF DESCRIPTION OF THE DRAWINGS

The foregoing and other objects and advantages of the invention will become apparent from the following detailed description of the invention when considered in conjunction with the accompanying drawings, in which like reference characters designate like parts throughout the several views, and wherein:

FIG. 1 is a somewhat schematic view, with parts shown in section, of an apparatus incorporating the features of the invention;

FIG. 2 is a longitudinal sectional view of the syringe of the invention, in which the taper of the side walls is shown exaggerated;

FIG. 4 is a longitudinal sectional view of the barrel of the syringe;

DETAILED DESCRIPTION OF THE PREFERRED EMBODIMENTS

Figure 3:
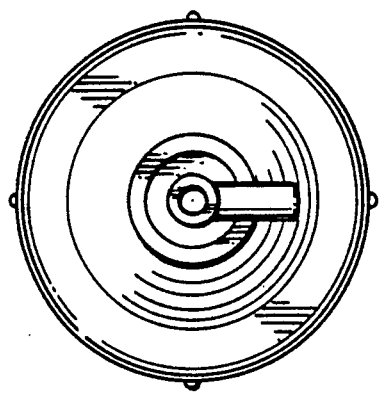
FIG. 3 is an end view of the syringe of FIG. 2, looking in the direction of the arrow 3.
Figure 6:
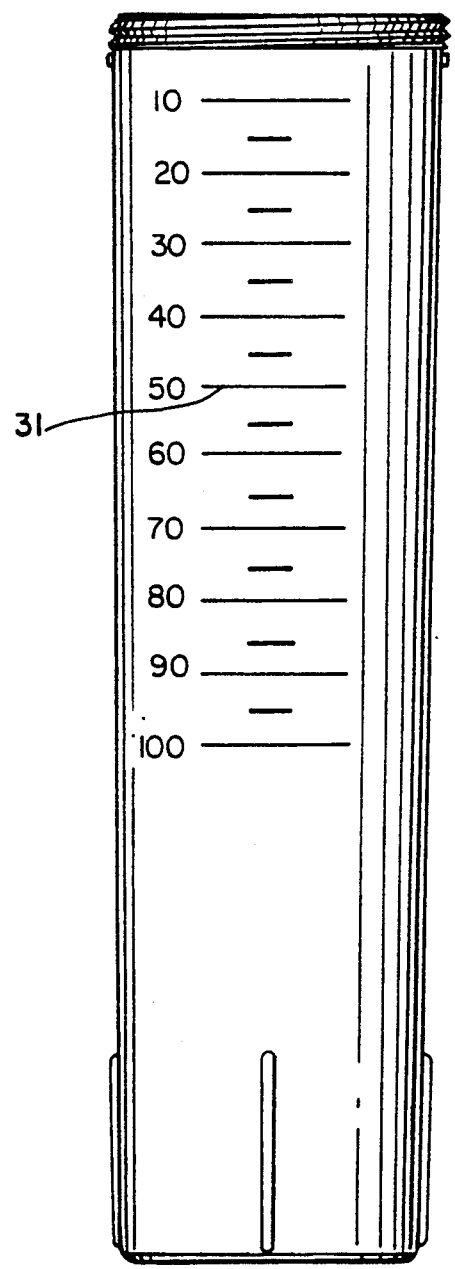
FIG. 6 is a side view in elevation of the barrel of the syringe used in the invention, showing the scale markings for visual observation of the quantity of drug administered.
Figure 5:
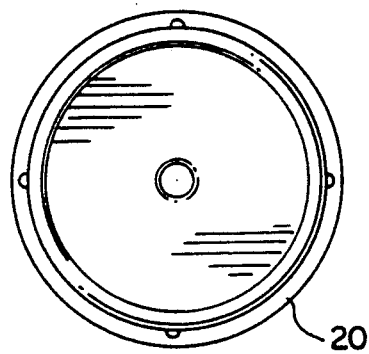
FIG. 5 is an end view of the barrel of FIG. 4, looking in the direction of the arrow 5.
Figure 7:
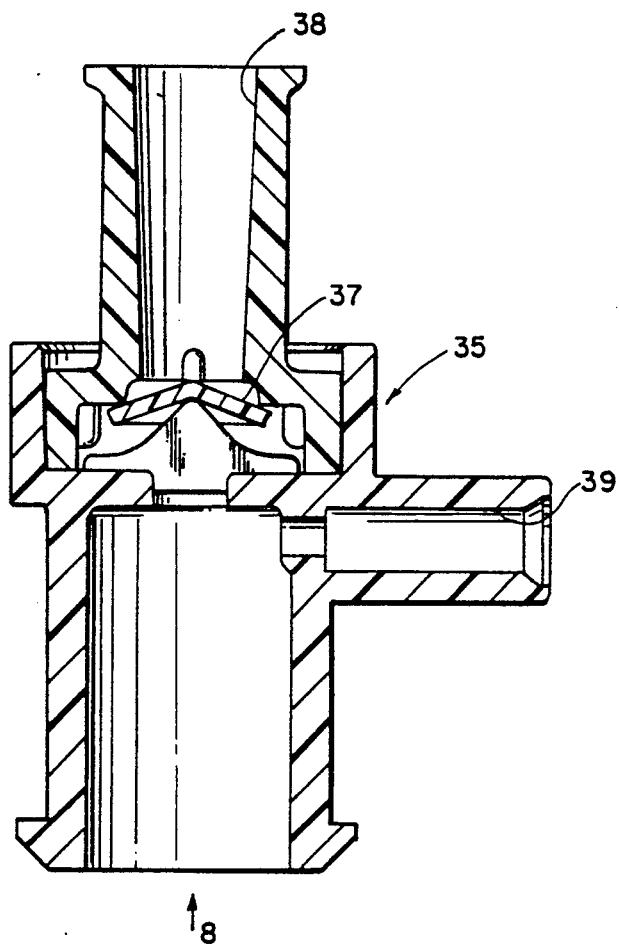
FIG. 7 is a greatly enlarged longitudinal sectional view of the one-way valve used in the device of the invention.
Figure 10:
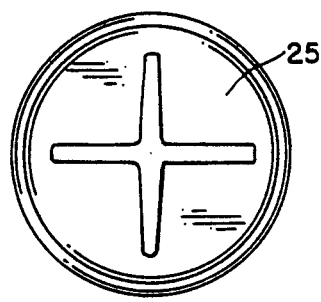
FIG. 10 is an end view of the piston of FIG. 9, looking in the direction of the arrow 10.
Figure 9:
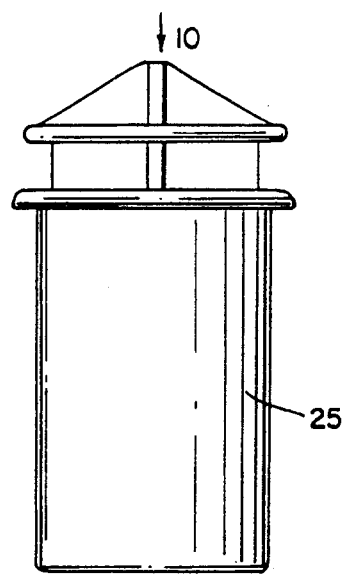
FIG. 9 is a greatly enlarged side view in elevation of the piston used in the syringe of the invention.
Figure 8:
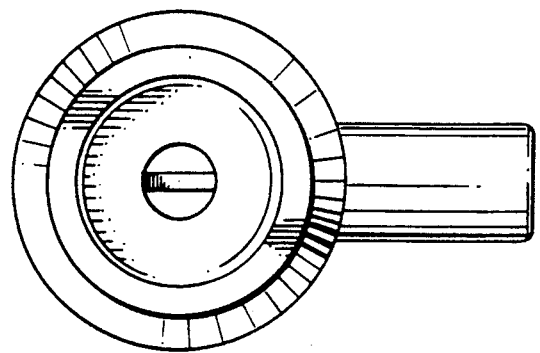
FIG. 8 is an end view of the valve of FIG. 7, looking in the direction of the arrow 8.

Referring more particularly to the drawings, a first form of apparatus according to the invention is shown generally at 10 in FIG. 1. The apparatus includes a syringe pump 11 connected through a one-way valve 12 with a length of tubing 13 having a slide clamp 14 thereon. In the form of invention shown in FIG. 1, a cone filter assembly 15 is attached to the distal end of the length of tubing and a combined needle adapter and restrictor 16 is attached to the cone filter. A needle 17 is attached to the adapter for piercing the vein of a patient for intravenous administration of a drug from the syringe.

With particular reference to FIGS. 1-5, the syringe pump 11 comprises a two-piece housing having a barrel 20 with a closed end 21 and an open end 22, with a top 23 attached to the open end. A piston 24 is reciprocal in the barrel and comprises a plastic plunger 25 having a rubber tip 26 for sliding engagement with the inner surface of the barrel wall. The piston is urged toward the open end of the barrel by a compression spring 27 engaged between the plastic plunger and the closed end of the barrel.

The syringe pump of the invention is distinct from prior art devices in that the barrel 20 has a reverse taper, being smaller in diameter at its closed end than at its open end, whereby the frictional drag on the piston becomes less as the spring expands and pushes the piston toward the open end of the barrel. In one specific construction model, the barrel has an inside diameter $D_1$ at its closed end of about 1.470 inches and an inside diameter $D_2$ at its closed end of about 1.510 inches, with a length L between the open and closed ends of about 6.325 inches. With this construction, the barrel has a taper per side of 0°, 10′, 45″, and the operative capacity of the syringe pump is about 105 cc. This taper on the barrel side wall is calculated to cooperate with the spring characteristics so that the reduction in force imparted by the expanding spring is compensated by the reduction in frictional drag between the piston and barrel side wall, achieving a constant force on the material being dispensed by the pump throughout the length of travel of the piston.

The separate cap or barrel top 23 enables the spring and piston to be assembled in the barrel, after which the cap is permanently affixed to the open end of the barrel.

An air vent filter 30 is placed in the closed end 21 of the barrel to vent air from the barrel as the piston is being forced to the bottom of the barrel during loading of the syringe, and also relieves vacuum in the barrel as the spring expands and pushes the piston upwardly in the barrel during a dispensing cycle.

The barrel is preferably transparent and has scale markings 31 thereon so that the quantity of drug in the syringe, and conversely, the quantity of drug administered may be visually observed.

A one-way T valve 35 is attached to the cap 23 for admitting drug to the syringe while it is being loaded, and through which the drug is dispensed during a dispensing cycle. This valve is snap-fitted to the cap 23 by snap detents 36, and includes a flexible disc 37 which functions as a one way valve to admit drug to the syringe through an inlet fitting 38 but which prevents reverse flow therethrough. Drug flows outwardly through the valve via an outlet port 39.

The length of tubing 13 is attached at its proximal end 13a to the outlet port 39, and the cone filter 15, needle adapter 16 and needle 17 are attached to the distal end 13b. Slide clamp 14 is placed on the tubing 13 between the ends for selectively interrupting flow. This would be done, for example, while filling the syringe through the one way valve.

Figure 11:
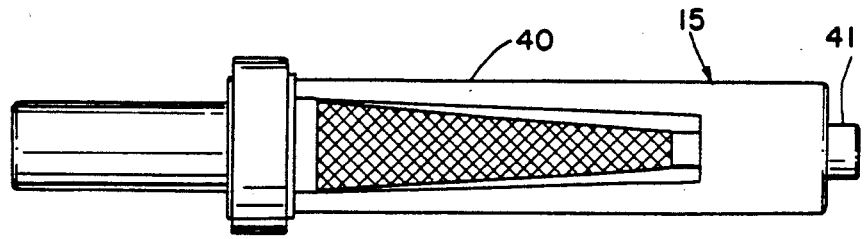
FIG. 11 is an enlarged view in side elevation of the cone filter used in on form of the invention.
Figure 12:
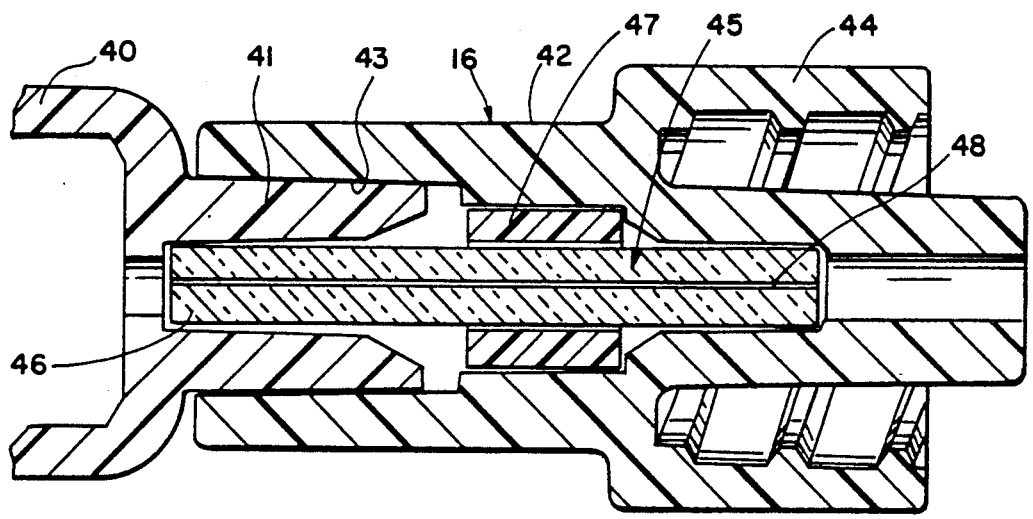
FIG. 12 is a greatly enlarged longitudinal sectional view of the cone filter of FIG. 11, with a restrictor according to a first form of the invention attached thereto.

In the form of the invention shown in FIGS. 1, 11 and 12, the cone filter assembly 15 comprises a housing 40 having the length of tubing attached at one end thereof and having a modified tip forming a male luer adapter 41 on its other end for attachment of the combined needle adapter and restrictor 16.

As seen best in FIG. 12, the combined needle adapter and restrictor 16 comprises a body 42 having a female luer adapter 43 on one end for cooperation with the male luer adapter on the cone filter housing. A solvent bond is placed between these two parts to secure them together. The other end of the body 42 is formed with a male luer lock fitting 44 for attachment of the needle 17.

The restrictor comprises a length of glass tube 45 secured within the body 42, and has one end 46 extending into the adjacent end of the cone filter housing and the other end extending into the body 42. A short section of extruded tubing 47 is positioned between the glass tube and the inside diameter of the body 42 to hold the glass tube in place during assembly and to effect a seal between the glass tube and body 42. A small diameter hole 48 is formed through the glass tube to form the restrictor for defining a regulated flow rate through the device. The length of the glass tube and the diameter of the hole 48 therethrough may be varied to achieve different regulated flow rates. For example, to achieve a flow rate of 200 ml/hr the tube may have a length of 0.500 inches and the hole 48 may have a diameter of 0.0080 inches; for a flow rate of 100 ml/hr, the tube may have a length of 0.300 inches and the hole a diameter of 0.0058 inches; for a flow rate of 5 ml/hr, the tube may have a length of 0.540 inches and the hole a diameter of 0.0030 inches; and for a flow rate of 2 ml/hr, the tube may have a length of 0.554 inches and the hole a diameter of 0.0024 inches. Other lengths and diameters may be chosen to achieve any desired flow rate, and these values are also related to the force exerted by the spring on the piston and the restriction to flow imposed by other components in the apparatus.

Figure 13:
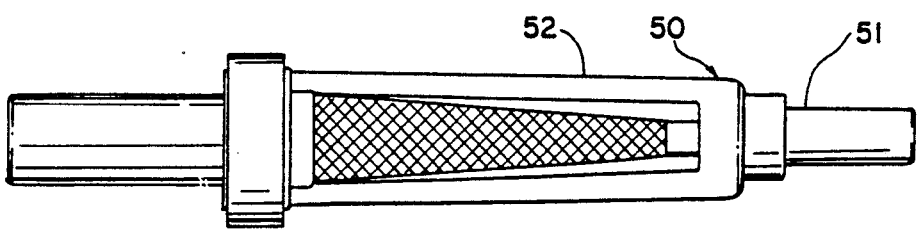
FIG. 13 is an enlarged view in side elevation of a second form of cone filter used in the device of the invention, wherein the restrictor comprises a laser-burned hole in the housing for the cone filter.
Figure 14:
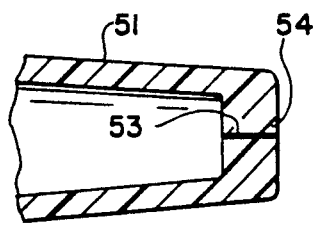
FIG. 14 is a greatly enlarged sectional view of the circled portion of FIG. 13, showing details of the laser-burned restrictor in the cone filter housing in this form of the invention.

A modified restrictor is shown at 50 in FIGS. 13 and 14. In this form of the invention, the end 51 of the cone filter housing 52 is extended and a laser-burned hole 53 is formed through the wall 54. To achieve a flow rate of 200 ml/hr in this form of the invention, the wall 54 is given a thickness of 0.040 inches and the hole 53 is given a diameter of 0.007 inches. This form of the invention is more economical to manufacture and assemble and requires fewer parts than the form previously described.

The cone filter may be eliminated in either of the forms of the invention described herein, if desired. In that event, the restrictor would be provided in a plastic fitting (not shown) attached to the distal end of the length of tubing 13.

In operation, the slide clamp 14 is closed and the liquid containing drug is forced through the one way valve 12 into the syringe, forcing the piston downwardly in the barrel and compressing the spring 27. Air behind the piston escapes through the air vent 30. When the syringe is filled, the slide clamp is opened to clear any air in the length of tubing 13. When the air has been cleared, the slide clamp is again closed. Thereafter, the needle 17 is inserted into the vein of a patient and the slide clamp opened to begin administration of the drug to the patient, with the flow rate being regulated by the restrictor 16 or 50.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

I claim:

1. In a liquid drug delivery device for administering a drug to a patient, wherein said drug delivery device includes pump means for containing and pressurizing a quantity of drug in liquid form to be delivered to a patient, a length of tubing connected at one end to the pump means for conveying drug from the pump means to the patient, and restrictor means in the length of tubing for regulating the flow rate of drug delivered therethrough from the pump means, the improvement wherein said pump means is a syringe pump, said syringe pump having a barrel with an outlet end and a piston reciprocal therein and a spring means engaged with said piston for urging said piston toward the outlet end to pressurize said drug and expel it from the syringe into the length of tubing, said barrel having a tapered side wall which increases in diameter toward the outlet end thereof, the degree of taper being chosen so as to produce varying piston drag which substantially compensates for decreasing spring force as the spring distends, and thereby produces a substantially constant pressure on the liquid, and thus a constant flow rate thereof regardless of piston position.

2. A syringe pump for pressurizing a fluid drug to be dispensed and administered to a patient, comprising:
    a barrel having an outlet end and a side wall;
    a piston reciprocable in the barrel and in sliding contact with the side wall of the barrel for pressurizing fluid in the barrel; and
    spring means engaged with the piston for urging it in a direction toward the outlet end to pressurize the fluid; wherein
    said barrel side wall is tapered between its ends so that it has a larger diameter at its outlet end, whereby the frictional resistance between the piston and barrel side wall becomes less as the spring expands and the piston moves toward the outlet end, the degree of taper being chosen so as to substantially compensate for decreased force imparted by the spring means as it expands, resulting in a constant force on the fluid during the entire length of travel of the piston in the barrel, whereby the flow rate of the fluid drug administered to the patient remains constant during an entire dispensing cycle.

3. A liquid drug delivery device for administering a drug to a patient at a constant and predetermined flow rate during a dispensing cycle, comprising:
    pump means for pressurizing the drug in liquid form;
    conduit means connected with the pump means for conveying the pressurized drug to the patient; and
    restrictor means fluidly connected with said pump means for regulating the flow rate of drug pressurized by the pump means and conveyed by the conduit means, said pump means having means for maintaining a constant pressure on the drug during an entire dispensing cycle to thereby obtain a constant flow rate of the drug during the dispensing cycle.

4. A drug delivery device as claimed in claim 2, wherein:
    said restrictor means comprises a length of glass tubing having a longitudinal opening therethrough.

5. A drug delivery device as claimed in claim 2, wherein:

said restrictor means comprises a laser-burned hole formed through a wall in a housing member inserted in said conduit means.

6. A drug delivery device as claimed in claim 2, wherein:

a filter means is in said conduit means for filtering contaminants from the fluid delivered to the patient, said filter means including a housing having one end attached to the conduit means and another end defining an adapter for attachment of a needle for insertion into the vein of the patient, said restrictor means being associated with said filter housing means.

7. A drug delivery device as claimed in claim 6, wherein:

said restrictor means comprises a length of glass tubing having a longitudinal opening therethrough, said glass tubing being confined within a needle adapter member attached to said filter housing.

8. A drug delivery device as claimed in claim 6, wherein:

said filter housing has an outlet end shaped with a transverse wall having a laser-burned hole formed therethrough and defining said restrictor means.

* * * * *